US011083509B2

(12) United States Patent
Kim

(10) Patent No.: US 11,083,509 B2
(45) Date of Patent: Aug. 10, 2021

(54) SCREW ANCHOR ASSEMBLY AND METHOD OF USING THE SAME IN PEDICLE SCREW FIXATION

(71) Applicant: KYUNGPOOK NATIONAL UNIVERSITY INDUSTRY-ACADEMIC COOPERATION FOUNDATION, Daegu (KR)

(72) Inventor: Kyoung Tae Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 15/608,828

(22) Filed: May 30, 2017

(65) Prior Publication Data

US 2017/0354442 A1 Dec. 14, 2017

(30) Foreign Application Priority Data

Jun. 8, 2016 (KR) ........................ 10-2016-0071012

(51) Int. Cl.
*A61B 17/84* (2006.01)
*A61B 17/68* (2006.01)
*A61B 17/70* (2006.01)
*A61B 17/86* (2006.01)

(52) U.S. Cl.
CPC .......... *A61B 17/844* (2013.01); *A61B 17/686* (2013.01); *A61B 17/7032* (2013.01); *A61B 17/8605* (2013.01); *A61B 17/7035* (2013.01); *A61B 17/8685* (2013.01)

(58) Field of Classification Search
CPC .............. A61B 17/844; A61B 17/8685; A61B 2017/8655; F16B 13/124; F16B 13/128
USPC ...................................... 606/313; 411/55, 71
See application file for complete search history.

(56) References Cited

U.S. PATENT DOCUMENTS

| 4,027,932 A | 6/1977 | Kunkel et al. |
| 4,359,318 A | 11/1982 | Gittleman |
| 4,474,516 A | 10/1984 | Schiefer |
| 4,678,383 A | 7/1987 | Bergner |
| 5,127,407 A | 7/1992 | Tan |
| 5,265,504 A | 11/1993 | Fruhm |
| 6,171,311 B1 | 1/2001 | Richelsoph |

(Continued)

FOREIGN PATENT DOCUMENTS

| JP | 2011-139901 A | 7/2011 |
| JP | 2014-517739 A | 7/2014 |

(Continued)

*Primary Examiner* — Amy R Sipp
(74) *Attorney, Agent, or Firm* — Novick, Kim & Lee, PLLC; Sang Ho Lee

(57) ABSTRACT

A screw anchor assembly used in pedicle screw fixation is provided. The screw anchor assembly includes a screw having screw threads defined on a circumferential surface, and a screw anchor having a first end and a second end, an accommodating part defined by anchor screw threads on an inner surface of the screw anchor and having one end to receive the screw, and a locking step extended in a circumferential direction from the first end of the screw anchor. The accommodating part flexibly extends when the screw is screw-coupled to the screw anchor.

8 Claims, 3 Drawing Sheets

(56) References Cited

U.S. PATENT DOCUMENTS

| | | |
|---|---|---|
| 6,249,946 B1 | 6/2001 | Greenhill |
| 6,258,089 B1 | 7/2001 | Campbell et al. |
| 6,290,701 B1 | 9/2001 | Enayati |
| 6,331,179 B1 | 12/2001 | Freid et al. |
| 6,402,757 B1 | 6/2002 | Moore, III et al. |
| 6,436,100 B1 | 8/2002 | Berger |
| 6,652,525 B1 | 11/2003 | Assaker et al. |
| 6,767,350 B1 | 7/2004 | Lob |
| 6,778,861 B1 | 8/2004 | Liebrecht et al. |
| 7,029,472 B1 | 4/2006 | Fortin |
| 7,194,314 B1 | 3/2007 | Richter et al. |
| 7,235,100 B2 | 6/2007 | Martinek |
| 7,302,298 B2 | 11/2007 | Lowry et al. |
| 7,662,154 B2 | 2/2010 | Ribeiro |
| 8,057,521 B2 | 11/2011 | Smisson, III et al. |
| 8,419,777 B2 | 4/2013 | Walker et al. |
| 8,454,667 B2 | 6/2013 | Humphreys |
| 8,628,325 B2 | 1/2014 | Vachtenberg |
| 8,758,347 B2 | 6/2014 | Weiner et al. |
| 8,906,077 B2 | 12/2014 | Bush, Jr. et al. |
| 8,932,335 B2 | 1/2015 | Humphreys |
| 8,940,030 B1 | 1/2015 | Stein et al. |
| 8,956,394 B1 | 2/2015 | Mcnonnell |
| 9,265,531 B2 | 2/2016 | Ziolo |
| 9,629,664 B2 | 4/2017 | Altarac et al. |
| 9,775,652 B2 | 10/2017 | Altarac et al. |
| 9,918,749 B2 | 3/2018 | Altarac et al. |
| 9,918,760 B2 | 3/2018 | Bush, Jr. et al. |
| 9,943,341 B2 | 4/2018 | Carnes et al. |
| 2002/0040241 A1 | 4/2002 | Jarvinen |
| 2002/0147454 A1* | 10/2002 | Neto ............... A61B 17/686 606/313 |
| 2002/0151899 A1 | 10/2002 | Bailey et al. |
| 2003/0135274 A1 | 7/2003 | Hays et al. |
| 2003/0187440 A1 | 10/2003 | Richelsoph et al. |
| 2004/0102828 A1* | 5/2004 | Lowry ............... A61N 1/0534 607/116 |
| 2004/0220571 A1 | 11/2004 | Assaker et al. |
| 2004/0243207 A1 | 12/2004 | Olson et al. |
| 2004/0267361 A1 | 12/2004 | Donnelly et al. |
| 2005/0059972 A1 | 3/2005 | Biscup |
| 2005/0192577 A1 | 9/2005 | Mosca et al. |
| 2005/0216027 A1 | 9/2005 | Suh |
| 2005/0261689 A1 | 11/2005 | Lin |
| 2006/0106390 A1* | 5/2006 | Jensen ............... A61B 17/8685 606/318 |
| 2006/0149258 A1 | 7/2006 | Sousa |
| 2006/0161157 A1 | 7/2006 | Mosca et al. |
| 2006/0217721 A1 | 9/2006 | Suh |
| 2006/0235410 A1 | 10/2006 | Ralph et al. |
| 2006/0247639 A1 | 11/2006 | Anderson |
| 2006/0293670 A1 | 12/2006 | Smisson et al. |
| 2007/0233071 A1 | 10/2007 | Dewey et al. |
| 2008/0039846 A1* | 2/2008 | Lee ............... A61B 17/686 606/63 |
| 2008/0161864 A1 | 7/2008 | Beck et al. |
| 2008/0188897 A1* | 8/2008 | Krebs ............... A61B 17/746 606/300 |
| 2008/0221624 A1 | 9/2008 | Gooch |
| 2009/0125072 A1 | 5/2009 | Neubardt |
| 2009/0318970 A1 | 12/2009 | Butler et al. |
| 2010/0036467 A1 | 2/2010 | Kraus et al. |
| 2010/0049256 A1 | 2/2010 | Jeon et al. |
| 2010/0106198 A1* | 4/2010 | Adcox ............... A61N 1/3605 606/301 |
| 2010/0121383 A1 | 5/2010 | Stanaford et al. |
| 2011/0022097 A1 | 1/2011 | Walker et al. |
| 2011/0029023 A1 | 2/2011 | Tornier |
| 2011/0106159 A1 | 5/2011 | Nazeck |
| 2011/0144702 A1 | 6/2011 | Leroux et al. |
| 2011/0152934 A1 | 6/2011 | Asaad et al. |
| 2011/0230885 A1 | 9/2011 | Weiner et al. |
| 2011/0264151 A1 | 10/2011 | Davis et al. |
| 2012/0185001 A1 | 7/2012 | Nayet et al. |
| 2012/0232595 A1 | 9/2012 | Holschlag |
| 2012/0265258 A1* | 10/2012 | Garvey ............... A61B 17/844 606/315 |
| 2012/0271363 A1 | 10/2012 | Luxon et al. |
| 2012/0289978 A1 | 11/2012 | Jacob |
| 2013/0023936 A1 | 1/2013 | Altarac et al. |
| 2013/0041413 A1 | 2/2013 | Sun |
| 2013/0231704 A1 | 9/2013 | Larroque-Lahitette |
| 2013/0304067 A1 | 11/2013 | Hess et al. |
| 2013/0325074 A1 | 12/2013 | Ziolo |
| 2014/0066997 A1 | 3/2014 | Humphreys |
| 2015/0134013 A1 | 5/2015 | Paul |
| 2015/0201982 A1 | 7/2015 | Altarac et al. |
| 2015/0216573 A1 | 8/2015 | Chin et al. |
| 2015/0230838 A1 | 8/2015 | Lazoglu et al. |
| 2016/0166295 A1 | 6/2016 | Ziolo |
| 2016/0206351 A1 | 7/2016 | Eom |
| 2016/0278834 A1* | 9/2016 | Bayer ............... A61B 17/863 |

FOREIGN PATENT DOCUMENTS

| | | |
|---|---|---|
| KR | 1999-0035953 A | 5/1999 |
| KR | 10-2002-0082009 A | 10/2002 |
| KR | 1020040001287 A | 1/2004 |
| KR | 20-0367241 Y1 | 11/2004 |
| KR | 10-2005-0023111 A | 3/2005 |
| KR | 10-2007-0026472 A | 3/2007 |
| KR | 10-2007-0112200 A | 11/2007 |
| KR | 10-2008-0059920 A | 7/2008 |
| KR | 10-0850322 B1 | 8/2008 |
| KR | 10-2008-0105506 A | 12/2008 |
| KR | 10-0872529 B1 | 12/2008 |
| KR | 10-2009-0015933 A | 2/2009 |
| KR | 10-2009-0111774 A | 10/2009 |
| KR | 10-2010-0124709 A | 11/2010 |
| KR | 10-2012-0039622 | 4/2012 |
| KR | 10-2012-0040309 A | 4/2012 |
| KR | 10-2012-0052265 A | 5/2012 |
| KR | 10-1142895 B1 | 5/2012 |
| KR | 10-2012-0057758 A | 6/2012 |
| KR | 10-2013-0004669 A | 1/2013 |
| KR | 10-2013-0015081 A | 2/2013 |
| KR | 10-2013-0016303 A | 2/2013 |
| KR | 10-1331429 B1 | 11/2013 |
| KR | 10-2014-0003938 A | 1/2014 |
| KR | 10-2014-0018796 A | 2/2014 |
| KR | 10-2014-0052320 A | 5/2014 |
| KR | 10-1413732 B1 | 7/2014 |
| KR | 10-2015-0120105 A | 10/2015 |
| WO | 2008/146981 A1 | 12/2008 |
| WO | 2009/105106 A2 | 8/2009 |

\* cited by examiner

SCREW ANCHOR ASSEMBLY AND METHOD OF USING THE SAME IN PEDICLE SCREW FIXATION

CROSS-REFERENCE TO RELATED APPLICATION

This application claims priority to and the benefit of Korean Patent Application No. 10-2016-0071012, filed on Jun. 8, 2016, the disclosure of which is incorporated herein by reference in its entirety.

BACKGROUND

The present disclosure relates to a screw anchor assembly and a method of using the same in pedicle screw fixation, and more particularly, to a screw anchor assembly having a structure capable of increasing fixation power for fixing a spinal bone and facilitating a surgery, and a method of using the screw anchor assembly in pedicle screw fixation.

Generally, for spinal conditions, an indirect therapy method using physical therapy and a direct therapy method in which a separate fixation device is installed at a damaged spinal segment to correct and fixate the spine are performed. That is, although physical therapy is performed when a spinal disease is not severe, therapy is performed using a separate spinal fixation device when a disease related to a cervical vertebra, a thoracic vertebra, a lumbar vertebra, a sacrum, and an intervertebral disc, which constitute the spine, is severe.

To return a damaged spinal segment to a normal functioning state and then fixate and stabilize the corrected spinal segment in order to prevent movement thereof, a commonly installed spinal fixation device includes a pedicle (sacrum) screw that is inserted into a pedicle or a sacrum of a vertebra at a predetermined angle and to a predetermined depth, a spinal rod disposed at one side of a spinal segment, and a fixation cap or a coupling and engaging part configured to connect and engage the spinal rod with the pedicle screw. To treat a damaged spinal segment, first, the pedicle screw is inserted and fixed to a pedicle or a sacrum of a vertebra in an appropriate position and direction, the spinal segment is corrected to the normal state using the spinal rod, the spinal rod and the pedicle screw are fixed using the fixation cap or the coupling and engaging part, and then treatment is finished.

Nowadays, due to an increase in the elderly population, the use of screw fixation in treating patients with severe osteoporosis has increased. However, in a case of conventional screw fixation (Korean Unexamined Patent Application Publication No. 10-2006-0133857), after screw fixation is performed, bone melting, which is referred to as a halo phenomenon, i.e., bone cavitation, may occur over time near a screw fixed to a bone. Due to this, loosening of the screw may occur. Consequently, because around half of patients who undergo screw fixation may later develop adjacent segment degeneration caused by the screw fixation and require revision surgery, a physical and economic burden may be placed on the patients.

In this case, a larger screw may be inserted into an area at which the screw loosening occurs, the bone near the screw may be filled with cement or the like, or an allograft bone plug may be inserted therein. However, it is difficult to reliably secure fixation power for fixing the screw to the bone by the above.

SUMMARY OF THE DISCLOSURE

To solve the above problems, the need for a screw anchor assembly that does not cause loosening of a screw after the screw is in place and fixed into the bone, and a method of using the screw anchor assembly in pedicle screw fixation is emerging.

It is an objective of the present disclosure to provide a screw anchor assembly that can be applied to screws of any length so that a surgery is facilitated and that has an increased contact area with a spinal bone and sufficient pullout strength so that a screw is reliably in place and fixed, and the physical toll can be reduced, along with lowering the cost of surgery, while also employing a method of using the screw anchor assembly in pedicle screw fixation.

Objectives of the present disclosure are not limited to that mentioned above, and other unmentioned objectives will be clearly understood by one of ordinary skill in the art from the description below.

To solve the above objectives, according to an embodiment of the present disclosure, a screw anchor assembly, which is a screw anchor assembly used in pedicle screw fixation, includes a screw having screw threads formed in a longitudinal direction, and a screw anchor inserted into a predetermined area of a spine and having anchor screw threads formed at an inner surface thereof that defines an accommodating part into which the screw is inserted so that the accommodating part is expanded during a process in which the screw anchor is screw-coupled to the screw, wherein a locking step is formed at one end of the screw anchor into which the screw is inserted so that the screw anchor is not drawn into an insertion space in the spine.

To attain the above objectives, according to an embodiment of the present disclosure, a method of using a screw anchor assembly in pedicle screw fixation includes inserting a screw anchor into a predetermined area of a spine, inserting an expanding member into an accommodating part defined by an inner surface of the screw anchor so that the screw anchor is attached to the inside of a spine by the expanding member being inserted into the accommodating part and expanding the accommodating part, and inserting a screw into the accommodating part of the screw anchor after removing the inserted expanding member, wherein a locking step is formed at one end of the screw anchor into which the screw is inserted so that the screw anchor is not drawn into an insertion space in the spine.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
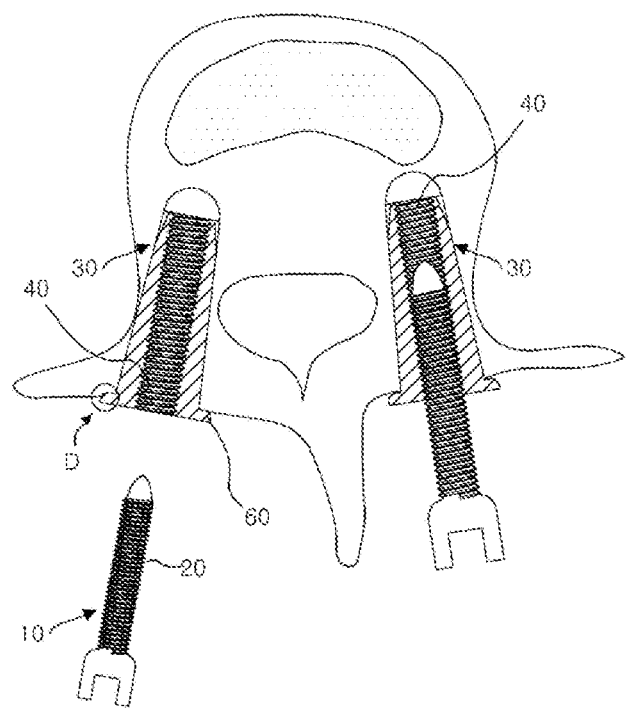
FIG. 1 is a view illustrating a process in which a screw anchor assembly is fixed within a spinal bone according to an embodiment of the present disclosure.

Advantages and features of the present disclosure and a method of achieving the same should become clear through embodiments described in detail below with reference to the accompanying drawings. However, the present disclosure is not limited to the embodiments disclosed below and may be realized in various other forms. The present embodiments make the disclosure of the present disclosure complete and are provided to completely inform one of ordinary skill in the art to which the present disclosure pertains of the scope of the disclosure. The present disclosure is defined only by the scope of the claims. Like reference numerals refer to like elements throughout.

Terms used herein are for describing the embodiments and are not intended to limit the present disclosure. In the specification, a singular expression includes a plural expression unless the context clearly indicates otherwise. The terms "comprises" and/or "comprising" used herein do not preclude the existence or the possibility of one or more additional elements, steps, and operations other than those mentioned.

Figure 2:
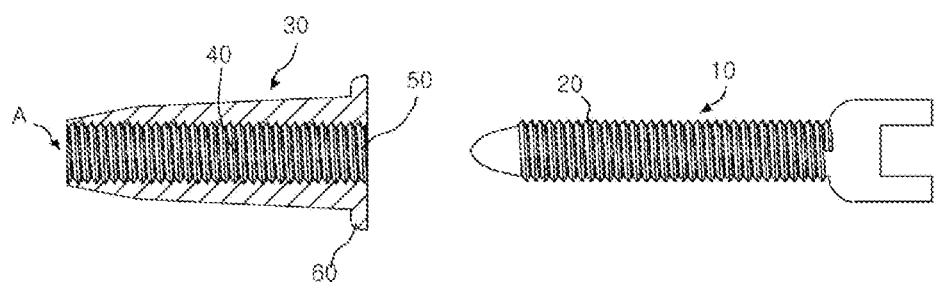
FIG. 2 is a view illustrating a state in which the screw anchor assembly is separated into a screw anchor and a screw according to an embodiment of the present disclosure.
Figure 3:
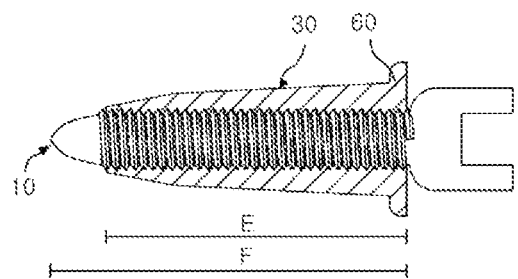
FIG. 3 is a view illustrating a state in which the screw anchor and the screw of the screw anchor assembly are coupled according to an embodiment of the present disclosure.

A screw anchor assembly according to an embodiment of the present disclosure will be described with reference to FIGS. 1 to 3. FIG. 1 is a view illustrating a process in which the screw anchor assembly is fixed within a spinal bone according to an embodiment of the present disclosure. FIG. 2 is a view illustrating a state in which the screw anchor assembly is separated into a screw anchor and a screw according to an embodiment of the present disclosure. FIG. 3 is a view illustrating a state in which the screw anchor and the screw of the screw anchor assembly are coupled according to an embodiment of the present disclosure.

Referring to FIGS. 1 to 3, the screw anchor assembly according to an embodiment of the present disclosure includes a screw anchor 30 and a screw 10.

The screw anchor 30 is a member that is inserted into a predetermined area of a spinal bone prior to the screw 10 instead of the screw 10 being immediately inserted into the area, and allows the screw 10 to be inserted into an accommodating part therein so that fixation power for fixing the screw 10 to the spinal bone is reinforced. For this, the screw anchor 30 has an accommodating part 50 formed therein and is configured to accommodate the screw 10 in a longitudinal direction.

Anchor screw threads 40 are formed on an inner surface that defines the accommodating part 50 of the screw anchor 30, the anchor screw threads 40 may be screw-coupled to screw threads 20 of the screw 10, which will be described below, and the screw 10 may be accommodated in the screw anchor 30 by such screw coupling. Damage to the screw anchor 30 and/or the screw 10 can be prevented when the screw 10 is inserted into the screw anchor 30 by screw coupling because pitches of the anchor screw threads 40 may be the same as pitches of the screw threads 20.

A locking step 60 may be formed at one end of the screw anchor 30, which is a part at which the coupling between the screw 10 and the screw anchor 30 begins (refer to D in FIG. 1), and the locking step 60 may be formed to expand from the one end of the screw anchor 30 outward or in a radial direction. In this way, the screw anchor 30 is not drawn into an insertion space in a spine even when the screw anchor 30 is inserted into the insertion space in the spine and the screw 10 is screw-coupled to the screw anchor 30 because the locking step 60 is present at the one end of the screw anchor 30. Consequently, the screw anchor 30 including the locking step 60 is fixed at an intended area and serves as an anchor.

In addition, a part of the locking step 60 that is in contact with the spine may be roughened, or a protrusion may be formed at the part of the locking step 60 in contact with the spine. Accordingly, a frictional force between the locking step 60 and the spine may be increased, and the role of the locking step as an anchor may be further strengthened.

Due to the presence of the locking step 60, fixation of the screw anchor assembly to a spinal bone is semi-permanent, and the fixation power is increased in comparison to a conventional case. Thus, a revision surgery recurrence decreases, and a physical and economic burden on a patient is reduced.

Also, the other end of the screw anchor 30, which is the opposite side of the one end thereof, may be open and have an opening A formed therein. As the opening A is formed in this manner, the screw 10 may pass through the opening A and protrude from the screw anchor 30 when the screw 10 is fixed to the spine through the screw anchor 30. That is, as illustrated in FIG. 3, even when a length F of the screw 10 is longer than a length E of the screw anchor 30, the length of the screw 10 does not need to be worried about much because the screw 10 can be fixed to the spine by being accommodated in the screw anchor 30. Accordingly, pedicle screw fixation can be promptly and conveniently performed.

Any material that is not harmful to the human body may be used as a material of the screw anchor 30. Although a plastic material such as polymethylmethacrylate (PMMA) may be used, development using calcium phosphate is planned nowadays, and any of polyether ether ketone (PEEK), a bone material, a bone substitute material, which is a material that is transformed into a bone over time, or an artificial bone may be used. Because the screw anchor 30 is formed with the above material, the screw anchor 30 is expanded and widened during a process in which the screw 10 is inserted thereinto. Accordingly, the screw anchor 30 may fill the insertion space in the spine and a coupling force with the spine may be increased, thereby improving fixation power for fixing the screw 10.

When an outer shape of the screw anchor 30 is examined, the screw anchor 30 may have a constant width from the one end to the other end, or may extend with a width gradually narrowing from the one end to the other end. In the latter, the screw anchor 30 can be easily inserted into the spine. However, the outer shape of the screw anchor is not limited to the above-described outer shapes, and may have any shape as long as the screw anchor can be easily inserted into the spine.

Further, after the screw anchor 30 is inserted in a predetermined area of the spine, instead of the screw 10 being immediately inserted into the accommodating part 50 of the screw anchor 30, an expanding member may be inserted into the accommodating part 50 of the screw anchor 30 so that the screw anchor 30 is expanded and an outer surface of the screw anchor 30 is attached to an inside of the spine. The inserted expanding member is removed after being inserted in this manner, and then the screw 10 is inserted into the accommodating part 50 of the screw anchor 30.

The screw 10 is a type of screw having the screw threads 20 formed in the longitudinal direction. The screw 10 is inserted into the screw anchor 30 by screw coupling and expands the accommodating part 50 of the screw anchor 30. Thus, the screw anchor 30 may be fixed to a spinal bone. As a result, the fixation of the screw anchor 30 fixes the screw 10 to the spinal bone and allows the spine to maintain a desired shape.

As described above, damage to the screw anchor 30 and/or the screw 10 may be prevented when the screw 10 is inserted into the screw anchor 30 by screw coupling because the pitches of the screw threads 20 and the anchor screw threads 40 may be the same.

Any material that is not harmful to the human body may be used as a material of the screw 10. Although a plastic material such as PMMA may be used, development using calcium phosphate is planned nowadays, and any of PEEK, a bone material, a bone substitute material, which is a material that is transformed into a bone over time, or an artificial bone may be used.

As illustrated in FIG. 1, pedicle screw fixation is performed using the screw anchor assembly including the above-described screw anchor 30 and screw 10. Specifically, to treat a damaged spinal segment, first, the screw anchor 30 is inserted and fixed to a pedicle or a sacrum of a vertebra in an appropriate position and direction, and a driver (not illustrated) is used to screw-couple the screw 10 to the accommodating part 50 of the inserted screw anchor 30.

Figure 4:
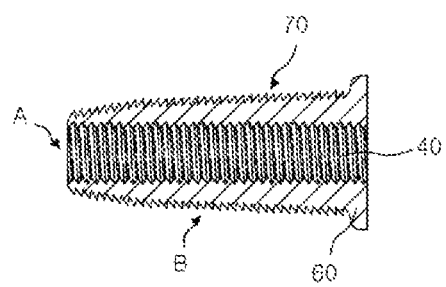
FIG. 4 is a cross-sectional view of a screw anchor of a screw anchor assembly according to another embodiment of the present disclosure.

The screw anchor assembly according to an embodiment of the present disclosure has been described above. Hereinafter, a screw anchor assembly according to another embodiment of the present disclosure will be described with reference to FIG. 4. FIG. 4 is a cross-sectional view of a screw anchor of a screw anchor assembly according to another embodiment of the present disclosure.

Unlike the screw anchor assembly according to the above-described embodiment of the present disclosure, the screw anchor assembly according to another embodiment of the present disclosure may include a locking part B formed along an entirety of or a part of an outer surface of a screw anchor 70. The locking part B may be a protrusion having an inclined surface, and the inclined surface of the locking part may be inclined toward another end of the screw anchor 70. In this way, due to the locking part B being formed at the outer surface of the screw anchor 70, a frictional coefficient and a contact area between the screw anchor 70 and a bone surface may be increased, and sufficient pullout strength may be obtained. As a result, a screw 10 inserted into the screw anchor 70 can be prevented from falling out of a bone.

Figure 5:
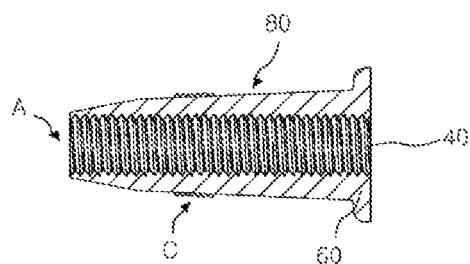
FIG. 5 is a cross-sectional view of a screw anchor of a screw anchor assembly according to still another embodiment of the present disclosure.

The screw anchor assemblies according to an embodiment and another embodiment of the present disclosure have been described above. Hereinafter, a screw anchor assembly according to still another embodiment of the present disclosure will be described with reference to FIG. 5. FIG. 5 is a cross-sectional view of a screw anchor of a screw anchor assembly according to still another embodiment of the present disclosure.

Referring to FIG. 5, a surface of a screw anchor 80 is roughened and includes a roughened outer surface C. Although the roughening is illustrated as being performed on only a part of the surface in FIG. 5, the entire surface of the screw anchor 80 can be roughened. Due to the roughened outer surface C, a frictional coefficient between the screw anchor 80 and a bone surface is increased, sufficient pullout strength is obtained, and fixation power of the screw anchor 80 is improved.

As mentioned above, conventionally, there is a problem in that revision surgery is required due to loosening of a screw over time after screw fixation is performed. However, by using the above screw anchor assembly according to the present disclosure, fixation of the screw 10 to the bone is reliably secured, and the conventional problem can be solved. Also, due to the opening A formed at other ends of the screw anchors 30, 70, and 80, pedicle screw fixation can be performed regardless of a length of the screw 10. Thus, the surgery is facilitated.

Figure 6:
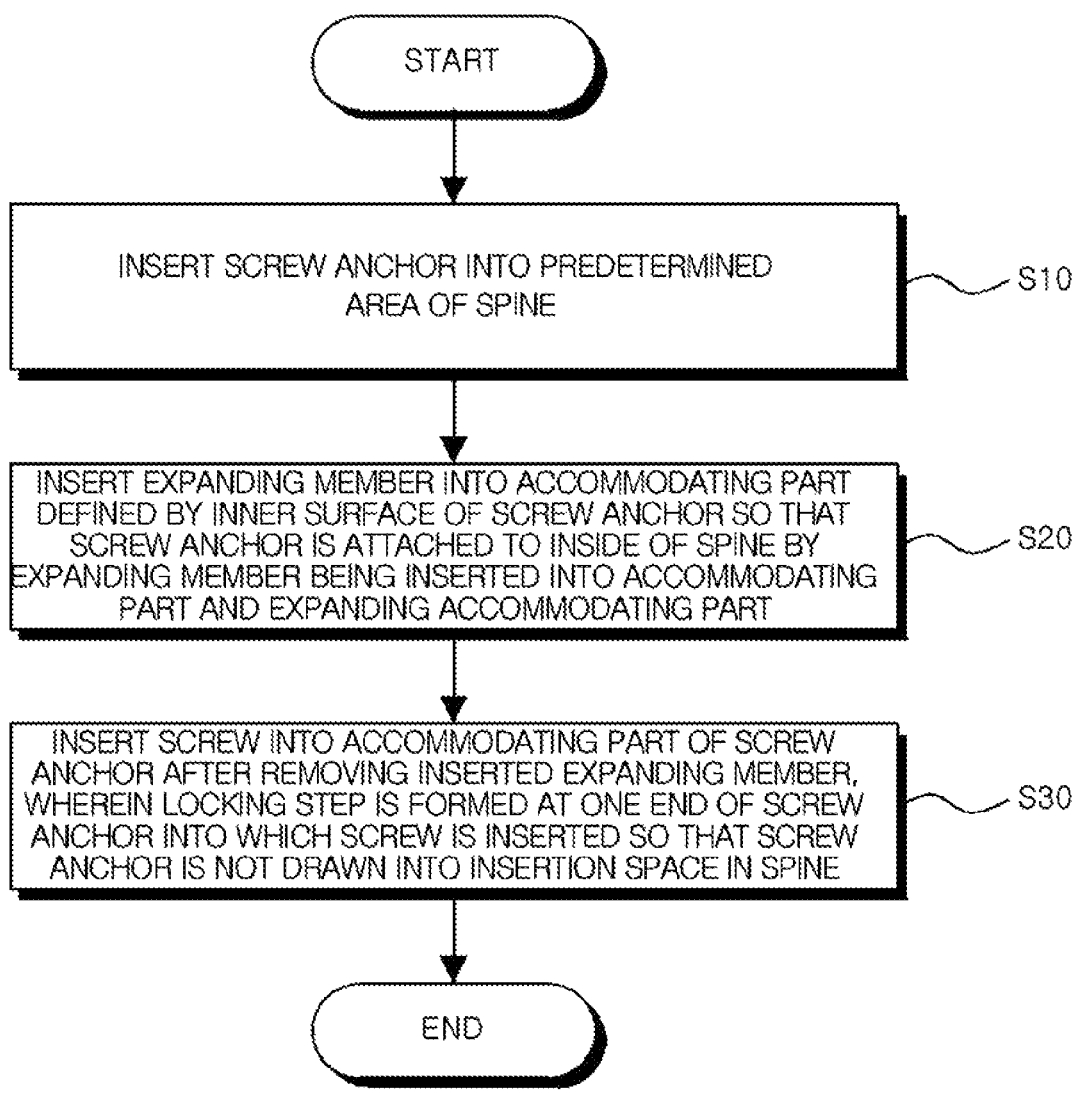
FIG. 6 is a flowchart of a method of using a screw anchor assembly in pedicle screw fixation according to an embodiment of the present disclosure.

The screw anchor assembly according to the present disclosure has been described above. Hereinafter, a method of using the screw anchor assembly according to an embodiment of the present disclosure in pedicle screw fixation will be described with reference to FIG. 6. FIG. 6 is a flowchart of a method of using a screw anchor assembly according to an embodiment of the present disclosure in pedicle screw fixation.

Referring to FIG. 6, the method of using the screw anchor assembly according to an embodiment of the present disclosure in pedicle screw fixation includes inserting a screw anchor into a predetermined area of a spine (S10), inserting an expanding member into an accommodating part defined by an inner surface of the screw anchor so that the screw anchor is attached to an inside of the spine by the expanding member being inserted into the accommodating part and expanding the accommodating part (S20), and inserting a screw into the accommodating part of the screw anchor after removing the inserted expanding member, wherein a locking step is formed at one end of the screw anchor into which the screw is inserted so that the screw anchor is not drawn into an insertion space in the spine (S30).

In the inserting of the screw anchor into the predetermined area of the spine (S10), the screw anchor 30 is inserted into a predetermined problem area of the spine.

In the inserting of the expanding member into the accommodating part so that the screw anchor is attached to the inside of the spine by the expanding member being inserted into the accommodating part defined by the inner surface of the screw anchor and expanding the accommodating part (S20), before the screw 10 is inserted into the accommodating part 50 of the screw anchor 30, the expanding member may be inserted into the accommodating part 50 of the screw anchor 30 to expand the screw anchor 30 and allow an outer surface of the screw anchor 30 to be attached to the inside of the spine. Accordingly, the inside of the screw anchor 30 is expanded, and the screw anchor 30 can be attached to an inner surface of the spine.

In the inserting of the screw into the accommodating part of the screw anchor after removing the inserted expanding member, wherein the locking step is formed at the one end of the screw anchor into which the screw is inserted so that the screw anchor is not drawn into the insertion space in the spine (S30), the screw 10 is inserted into the accommodating part 50 of the screw anchor 30 after removing the inserted expanding member, and here, the locking step 60 is present at the one end of the screw anchor 30 so that the locking step 60 is locked at a spinal segment near the insertion space in the spine and the screw anchor 30 is not drawn into the insertion space.

According to the present disclosure, a screw anchor assembly that can be applied to screws of any length so that surgery is facilitated and that has an increased contact area with a spinal bone and sufficient pullout strength so that a screw is reliably fixed and a physical and economic burden is not placed on a patient, and a method of using the screw anchor assembly in pedicle screw fixation can be provided.

Although embodiments of the present disclosure have been described above with reference to the accompanying drawings, one of ordinary skill in the art to which the present disclosure pertains should understand that the present disclosure can be performed in other specific forms without changing the technical spirit or essential features thereof.

Therefore, the above-described embodiments are illustrative in all aspects and are not to be understood as limiting.

What is claimed is:

1. A screw anchor assembly for use in pedicle screw fixation, the screw anchor assembly comprising:
   a screw including:
      a head portion configured to receive a tool to be rotated and located at a proximal end,
      an unthreaded portion located at a distal end thereof, wherein the unthreaded portion is rounded, and
      a body portion extending between the head portion and the unthreaded portion, wherein screw threads are arranged on an entire circumferential surface of the body portion and extend between the head portion and the unthreaded portion; and
   a screw anchor including:
      a first end and a second end spaced along a longitudinal direction,
      a point located between the first end and the second end,
      a through-hole penetrating the first end and the second end, and
      a locking step extending in a circumferential direction from the first end of the screw anchor,
   wherein the through-hole comprises anchor screw threads on an entire inner surface of the through-hole, the through-hole being configured to accommodate the screw,
   wherein a longitudinal length of the anchor screw threads is similar to a longitudinal length of the screw threads,
   wherein the screw anchor flexibly extends when the screw is screw-coupled to the screw anchor,
   wherein the screw anchor extends with a width gradually narrowing from the first end to the point with a first slope and gradually narrowing from the point to the second end with a second slope, and the second slope is greater than the first slope,
   wherein a diameter of the locking step is greater than a diameter of the head portion, the diameter of the head portion is greater than a diameter of the through-hole,
   wherein, when the screw is completely coupled to the screw anchor, an entire surface of the unthreaded portion of the screw protrudes from the second end of the screw anchor, while substantially all of the screw threads of the body portion are coupled with the anchor screw threads of the through-hole, and
   wherein the unthreaded portion extends to the distal end with a width gradually narrowing with a third slope which is similar to the second slope, and
   wherein a material of the screw includes any one of polymethylmethacrylate (PMMA), calcium phosphate, polyether ether ketone (PEEK), and a bone material.

2. The screw anchor assembly of claim 1, wherein a material of the screw anchor includes any one of polymethylmethacrylate (PMMA), calcium phosphate, polyether ether ketone (PEEK), and a bone material.

3. The screw anchor assembly of claim 1, wherein a part of the locking step has a roughened surface.

4. The screw anchor assembly of claim 1, wherein at least one protrusion is disposed on the locking step.

5. The screw anchor assembly of claim 1, wherein the screw is configured to be fixed to a spine through the screw anchor.

6. The screw anchor assembly of claim 1, wherein a pitch of the screw thread and a pitch of the anchor screw thread are the same.

7. The screw anchor assembly of claim 1, wherein the screw threads of the screw are configured to be coupled with the anchor screw threads of the screw anchor that has an outer surface configured to be attached to an inside of a spine.

8. The screw anchor assembly of claim 1, wherein the head portion extends in a first direction and the locking step extends normal to the first direction.

* * * * *